United States Patent
Wollin et al.

(10) Patent No.: US 9,713,614 B2
(45) Date of Patent: Jul. 25, 2017

(54) COMBINATION OF HMG-COA REDUCTASE INHIBITORS WITH PHOSPHODIESTERASE 4 INHIBITORS FOR THE TREATMENT OF INFLAMMATORY PULMONARY DISEASES

(71) Applicant: TAKEDA GMBH, Konstanz (DE)

(72) Inventors: Stefan-Lutz Wollin, Bad Waldsee (DE); Andrea Wohlsen, Neuchatel (CH); Clemens Braun, Konstanz (DE); Degenhard Marx, Moos (DE)

(73) Assignee: ASTRAZENECA AB, Södertalje (SE)

( * ) Notice: Subject to any disclaimer, the term of this patent is extended or adjusted under 35 U.S.C. 154(b) by 0 days.

(21) Appl. No.: 14/719,948

(22) Filed: May 22, 2015

(65) Prior Publication Data

US 2015/0272949 A1    Oct. 1, 2015

Related U.S. Application Data (63) Continuation of application No. 12/308,878, filed as application No. PCT/EP2007/056683 on Jul. 3, 2007, now abandoned.

(30) Foreign Application Priority Data

Jul. 5, 2006 (EP) .................................. 06116625

(51) Int. Cl.
| | |
|---|---|
| *A61K 31/505* | (2006.01) |
| *A61K 31/44* | (2006.01) |
| *A61K 31/4425* | (2006.01) |
| *A61K 31/22* | (2006.01) |
| *A61K 31/277* | (2006.01) |
| *A61K 31/343* | (2006.01) |
| *A61K 31/352* | (2006.01) |
| *A61K 31/366* | (2006.01) |
| *A61K 31/40* | (2006.01) |
| *A61K 31/405* | (2006.01) |
| *A61K 31/437* | (2006.01) |
| *A61K 31/4439* | (2006.01) |
| *A61K 31/453* | (2006.01) |
| *A61K 31/502* | (2006.01) |
| *A61K 45/06* | (2006.01) |

(52) U.S. Cl.
CPC ............ *A61K 31/505* (2013.01); *A61K 31/22* (2013.01); *A61K 31/277* (2013.01); *A61K 31/343* (2013.01); *A61K 31/352* (2013.01); *A61K 31/366* (2013.01); *A61K 31/40* (2013.01); *A61K 31/405* (2013.01); *A61K 31/437* (2013.01); *A61K 31/44* (2013.01); *A61K 31/4425* (2013.01); *A61K 31/4439* (2013.01); *A61K 31/453* (2013.01); *A61K 31/502* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,346,227 A | 8/1982 | Tanaka et al. | |
| 6,953,853 B2 | 10/2005 | Grundler et al. | |
| 7,178,910 B2 | 2/2007 | Suzuki et al. | |
| 7,531,540 B2 | 5/2009 | Grundler et al. | |
| 2002/0103226 A1 | 8/2002 | Deschenes et al. | |
| 2002/0143032 A1 | 10/2002 | Macdonald et al. | |
| 2002/0198136 A1 | 12/2002 | Mak et al. | |
| 2003/0096829 A1 | 5/2003 | Li et al. | |
| 2004/0162314 A1 | 8/2004 | Dube et al. | |
| 2004/0167199 A1 | 8/2004 | Muller et al. | |
| 2004/0254238 A1 | 12/2004 | Garrett et al. | |
| 2005/0119330 A1 | 6/2005 | Kao et al. | |
| 2005/0234068 A1 | 10/2005 | Baldwin | |
| 2006/0004056 A1 | 1/2006 | Cote et al. | |
| 2006/0094723 A1 | 5/2006 | Dunkern et al. | |
| 2006/0142308 A1* | 6/2006 | Kolassa ............... | A61K 31/167 514/262.1 |
| 2006/0148721 A1 | 7/2006 | Erondu | |
| 2006/0160834 A1 | 7/2006 | Fong et al. | |
| 2006/0223850 A1 | 10/2006 | Dube et al. | |
| 2007/0208029 A1 | 9/2007 | Barlow et al. | |
| 2008/0070940 A1 | 3/2008 | Dube et al. | |
| 2008/0103105 A1 | 5/2008 | Barlow et al. | |

FOREIGN PATENT DOCUMENTS

| | | |
|---|---|---|
| DE | 3122499 C2 | 12/1981 |
| EP | 0022478 B1 | 1/1981 |
| EP | 0033538 B1 | 8/1981 |
| EP | 0114027 B1 | 7/1984 |
| EP | 0247633 B1 | 12/1987 |
| EP | 0304063 B1 | 2/1989 |
| EP | 0307342 A2 | 3/1989 |
| EP | 0380392 B1 | 8/1990 |
| EP | 0521471 B1 | 1/1993 |
| EP | 0731099 B1 | 9/1996 |

(Continued)

OTHER PUBLICATIONS

Timmer et al. in J. Clin. Pharmacol. 42, 297-303 (2002).*
Timmer, et al., "The New Phosphodiesterase 4 Inhibitor Roflumilast is Efficacious in Exercise-Induced Asthma and Leads to Suppression of LPS-Stimulated TNF-a Ex Vivo", J Clin Pharmacol, 2002, vol. 42, pp. 297-303.
Kwak, et al., "Roflumilast Inhibits Lipopolysaccharide-Induced Inflammatory Midiators via Suppression of Nuclear Factors-kB, p38 Mitogen-Activated Protein Kinase, and c-Jun NH2-Terminal Kinase Activation", The Journal of Pharmacology and Experimental Therapeutics, 2005, vol. 315, No. 3, pp. 1188-1195.

(Continued)

*Primary Examiner* — Dennis Heyer
(74) *Attorney, Agent, or Firm* — Nath, Goldberg & Meyer; Joshua B. Goldberg; Scott H. Blackman (57) ABSTRACT

The invention relates to the combined use of a PDE4 inhibitor with a HMG-CoA reductase inhibitor for the prevention and curative treatment of an inflammatory pulmonary disease.

6 Claims, 2 Drawing Sheets

(56) References Cited

FOREIGN PATENT DOCUMENTS

| | | |
|---|---|---|
| EP | 1275388 A1 | 1/2003 |
| JP | 08/512041 A | 12/1996 |
| JP | 2001294526 A | 10/2001 |
| JP | 2004/512278 A | 4/2004 |
| JP | 2004/518727 A | 6/2004 |
| JP | 2007/508508 A | 4/2007 |
| WO | 8905639 A1 | 6/1989 |
| WO | 9209586 A1 | 6/1992 |
| WO | 93/19749 A1 | 10/1993 |
| WO | 95/01338 A1 | 1/1995 |
| WO | 9639408 A1 | 12/1996 |
| WO | 9809946 A1 | 3/1998 |
| WO | 9955696 A1 | 11/1999 |
| WO | 0048626 A2 | 8/2000 |
| WO | 01/19357 A2 | 3/2001 |
| WO | 01/46151 A1 | 6/2001 |
| WO | 0170738 A2 | 9/2001 |
| WO | 02/24194 A2 | 3/2002 |
| WO | 02/064584 A1 | 8/2002 |
| WO | 03/028730 A2 | 4/2003 |
| WO | 03070279 A1 | 8/2003 |
| WO | 2004/048374 A1 | 6/2004 |
| WO | 2004/089940 A1 | 10/2004 |
| WO | 2004/098578 A2 | 11/2004 |
| WO | 2005000217 A2 | 1/2005 |
| WO | 2005102317 A1 | 11/2005 |
| WO | 2005/115462 A1 | 12/2005 |
| WO | 2006/008437 A1 | 1/2006 |
| WO | WO2006/008437 * | 1/2006 |
| WO | 2006032676 A1 | 3/2006 |
| WO | 2006/117534 A2 | 11/2006 |
| WO | 2006/123125 A1 | 11/2006 |
| WO | 2006/132091 A1 | 12/2006 |
| WO | 2007/047978 A2 | 4/2007 |
| WO | 2007/048225 A1 | 5/2007 |
| WO | 2007/054789 A1 | 5/2007 |

OTHER PUBLICATIONS

Profita, et al., "Effect of Cilomilast (Ariflo) on Tnf-a, IL-8, and GM-CSF Release by Airway Cells of Patients with COPD", Thorax, 2003, vol. 58, pp. 573-579.

Draheim, et al., "Anti-Inflammatory Potential of the Selective Phosphodiesterase 4 Inhibitor N-(3,5-Dichloro-pyrid-4-yl)-[1-(4-fluorobenzyl)-5-hydroxy-indole-3-yl]-glyoxylic Acid Amide (AWD 12-281), in Human Cell Preparations", The Journal of Pharmacology and Experimental Therapeutics, 2004, vol. 308, No. 2, pp. 555-563.

Gamble et al. "Antiinflannmatory Effects of the Phosphodiesterase-4 Inhibitor Cilomilast (Ariflo) in Chronic Obstructive Pulmonary Disease", American Journal of Respiratory and Critical Care Medicine, vol. 168, 2003, pp. 976-982.

Crisby, M., "Modulation of the inflammatory process by statins," Timely Topics in Medicine. Cardiovascular Diseases, vol. 9, E3 (Mar. 1, 2005).

Kalinowski, L. et al., "Cerivastatin Potentiates Nitric Oxide Release and eNOS Expression through Inhibition of Isoprenoids Synthesis," Journal of Physiology and Pharmacology, vol. 53:4, pp. 585-595 (2002).

Lee, J. et al., "Simvastatin Inhibits Cigarette Smoking-induced Emphysema and Pulmonary Hypertension in Rat Lungs," American Journal of Respiratory and Critical Care Medicine, vol. 172, pp. 987-993 (2005).

McKay, A. et al., "A Novel Anti-Inflammatory Role of Simvastatin in a Murine Model of Allergic Asthma," The Journal of Immunology, vol. 172, pp. 2903-2908 (2004).

Mulhaupt, F. et al., "Statins (HMG-CoA reductase inhibitors) reduce CD40 expression in human vascular cells," Cardiovascular Research, vol. 59, pp. 755-766 (2003).

Stoll, L. et al., "Antioxidant Effects of Statins," Drugs of Today, vol. 40:12, pp. 975-990 (2004).

Veillard, N.R. et al., "Simvastatin modulates chemokine and chemokine receptor expression by geranylgeranyl isoprenoid pathway in human endothelial cells and macrophages," Atherosclerosis, (Nov. 28, 2005).

Watts, K.L. et al., "Simvastatin Inhibits Growth Factor Expression and Modulates Profibrogenic Markers in Lung Fibroblasts," American Journal of Respiratory Cell and Molecular Biology, vol. 32, pp. 290-300 (2005).

Ascer et al. in Atherosclerosis 177 (2004) 161-166.

National Heart Lung and Blood Institute (www.nhlbi.nih.gov/health/dci/Diseases/Copd/Copd_All.html).

www.merriam-webster.com/dictionary/cure.

www.merriam-webster.com/dictionary/prevent.

Written Opinion of the International Searching Authority Report issued in International Application No. PCT/EP2007/056683 dated Jul. 3, 2007 (Jul. 3, 2007).

International Search Report issued in International Application No. PCT/EP2007/056683 dated Jan. 25, 2008 (Jan. 25, 2008).

* cited by examiner

Figure 1: Inhibition of LPS-induced (systemic) TNFα release in rats by COMPOUND A Figure 2: Inhibition of LPS-induced (systemic) TNFα release in rats by ATORVASTATIN hemi-calcium sesqui-hydrate Figure 3: Inhibition of LPS-induced (systemic) TNFα release in rats by a combination of COMPOUND A and ATORVASTATIN hemi-calcium sesqui-hydrate

COMBINATION OF HMG-COA REDUCTASE INHIBITORS WITH PHOSPHODIESTERASE 4 INHIBITORS FOR THE TREATMENT OF INFLAMMATORY PULMONARY DISEASES

This application was filed as a continuation of application Ser. No. 12/308,878, filed Dec. 29, 2008 and since abandoned, which was filed under 35 U.S.C. 371 as a national stage of PCT/EP2007/056683, filed Jul. 3, 2007, and which claimed priority to EP 06116625, filed Jul. 5, 2006.

TECHNICAL FIELD

The present invention relates to the combination of certain known therapeutic compounds for therapeutic purposes. The substances used in the combinations according to the invention are known active agents from the phosphodiesterase 4 (PDE4) inhibitor class and active agents from the HMG-CoA-reductase inhibitor class.

BACKGROUND ART

Statins are widely used as cholesterol lowering therapeutic agents. They reduce cholesterol levels through competitive inhibition of 3-hydroxy-3-methylglutaryl coenzyme A (HMG-CoA) reductase, the key enzyme that regulates cholesterol synthesis. The cholesterol-lowering effect of statins is also due to an increase in the uptake of cholesterol by cells as a result of intracellular cholesterol depletion and enhanced expression of low-density lipoprotein (LDL) receptors.

However, statins exhibit properties that are beyond their lipid-lowering effects. These non-lipid-lowering properties involve the inhibition of the isoprenoid pathway including the cholesterol precursor mevalonate which is required as a precursor for the prenylation of a number of proteins leading to a change in function [Drugs of Today; 2004; 40: 975-990]. For example simvastatin modulates chemokine and chemokine receptor expression by geranylgeranyl isoprenoid pathway in human endothelial cells and macrophages [Veillard N R et al; Simvastatin modulates chemokine and chemokine receptor expression by geranylgeranyl isoprenoid pathway in human endothelial cells and macrophages; Atherosclerosis; 2005 Nov. 28; Epub ahead of print]. Statins also have a potential role as antioxidants leading to downregulation of inflammation [Drugs of Today; 2004; 40: 975-990]. Recent research data demonstrated that statins inhibit the induction of the major histocompatibility (MHC) class II expression by interferon-gamma (IFN-gamma), leading to repression of MHC II-mediated T-cell activation. Furthermore, statins inhibit the expression of specific cell surface receptors on monocytes, adhesion molecules and also integrin-dependent leucocyte adhesion [Timely Top Med Cardiovasc Dis; 2005; 9: E3]. Statins exhibit additional effects on inflammation by decreasing IL-6, IL-8, and MCP-1 synthesis in human vascular smooth muscle cells (VSMC) in vitro [Cardiovas Res; 2003; 59: 755-66]. Simvastatin inhibits growth factor expression and modulates profibrogenic markers in lung fibroblasts [Am J Respir Cell Mol Biol. 2005; 32: 290-300]. Furthermore, statins increase bioavailability of nitric oxide. Cerivastatin increased eNOS expression a NO release in human endothelial cells [J Physiol Pharmacol. 2002; 53:585-95]. In vivo statins exert anti-inflammatory effects in many models of inflammatory airway diseases like asthma and COPD. Simvastatin was shown to inhibit pulmonary inflammatory cell accumulation and IL-4 and IL-5 release into the alveolar lumen after allergen challenge in mice [J Immunol. 2004; 172: 2903-8]. Simvastatin inhibits cigarette smoking-induced emphysema and pulmonary hypertension in rat lungs [Am J Respir Crit Care Med. 2005; 172: 987-93]. Overall statins exhibit inhibitory properties on inflammation and modulation on the immune system.

In the international patent application WO00/48626 (University of Washington) aerosol compositions of HMG-CoA reductase inhibitors for inhibiting inflammation associated with a pulmonary disease, such as asthma, interstitial pneumonitis, emphysema, chronic bronchitis, adult respiratory distress syndrome (ARDS) and cystic fibrosis, are described. In EP1275388 (Takeda) several statins are described as useful for the treatment of TNFα associated diseases such as inflammatory diseases including asthma and COPD. In US20050119330 the use of HMG-CoA reductase inhibitors is described for the treatment of lung proliferative vascular disorders, such as for example, pulmonary hypertension and pulmonary fibrosis.

There is pressing need to improve the treatment of inflammatory pulmonary diseases like asthma and COPD. These inflammatory diseases are characterized by multifactorial pathologies. Several inflammatory mediators are involved as well as various cell types. Therefore, in medical practice for the treatment of e.g. asthma and COPD the targeting of a single mediator or cell type has not lead to satisfactory results. For both asthma and COPD at present combination therapies are used but in many instances with limited success especially in COPD.

Cyclic nucleotide phosphodiesterase (PDE) inhibitors, particularly inhibitors of type 4 (PDE4), are useful in the treatment of a variety of allergic and inflammatory diseases, for example in respiratory diseases, such as asthma and chronic obstructive pulmonary disease.

HMG-CoA reductase inhibitors, by a route different from PDE4 inhibitors, are also useful in the treatment of inflammatory diseases.

It would be desirable to provide combinations and methods of treatment that can take advantage of the different therapeutic pathways of a PDE4 inhibitor and a HMG-CoA reductase inhibitor to more effectively treat inflammatory disorders, in particular asthma and COPD.

DESCRIPTION OF THE INVENTION

It has now been found that the combined use of a PDE4 inhibitor and a HMG-CoA reductase inhibitor potentiates the anti-inflammatory effect of either component alone.

Therefore, according to a first aspect of the present invention there is provided a pharmaceutical composition comprising a pharmaceutical formulation including an amount of a PDE4 inhibitor or a pharmaceutically acceptable salt thereof, an amount of a HMG-CoA reductase inhibitor or a pharmaceutically acceptable salt thereof, wherein the first amount and the second amount together comprise an effective amount for the preventive or curative treatment of an inflammatory pulmonary disease, and at least one pharmaceutically acceptable auxiliary.

The above-mentioned pharmaceutical composition provides for the administration of a PDE4 inhibitor or a pharmaceutically acceptable salt thereof with a HMG-CoA reductase inhibitor or a pharmaceutically acceptable salt thereof and is thus presented as a single formulation.

Alternatively, the PDE4 inhibitor or a pharmaceutically acceptable salt thereof and the HMG-CoA reductase inhibitor or a pharmaceutically acceptable salt thereof may be presented as separate formulations, wherein at least one of those formulations comprises a PDE4 inhibitor or a pharmaceutically acceptable salt thereof and at least one comprises a HMG-CoA reductase inhibitor or a pharmaceutically acceptable salt thereof.

Thus, there is further provided:

A combination product comprising the components: (A) an amount of a PDE4 inhibitor or a pharmaceutically acceptable salt thereof; (B) an amount of a HMG-CoA reductase inhibitor or a pharmaceutically acceptable salt thereof; wherein the first and the second amount together comprise an effective amount for the preventive or curative treatment of an inflammatory pulmonary disease and wherein each of the components (A) and (B) is formulated in admixture with at least one pharmaceutically acceptable auxiliary.

A kit comprising the components: (A) a pharmaceutical formulation including an amount of a PDE4 inhibitor or a pharmaceutically acceptable salt thereof, in admixture with at least one pharmaceutically acceptable auxiliary; (B) a pharmaceutical formulation including an amount of a HMG-CoA reductase inhibitor or a pharmaceutically acceptable salt thereof, in admixture with at least one pharmaceutically acceptable auxiliary; wherein the first and the second amount together comprise an effective amount for the preventive or curative treatment of an inflammatory pulmonary disease.

The combinations according to the invention can be used for the preventive or curative treatment of inflammatory pulmonary diseases, such as, for example, asthma, COPD, sclerosis, alveolitis, sarcoidosis, idiopathic pulmonary fibrosis and pulmonary hypertension.

Therefore, further aspects of the invention are:

Combination of a PDE4 inhibitor or a pharmaceutically acceptable salt thereof and a HMG-CoA reductase inhibitor or a pharmaceutically acceptable salt thereof for use as a medicament.

Combination of a PDE4 inhibitor or a pharmaceutically acceptable salt thereof and a HMG-CoA reductase inhibitor or a pharmaceutically acceptable salt thereof for the preventive or curative treatment of an inflammatory pulmonary disease.

Pharmaceutical composition, combination product or kit, as described in the preceding paragraphs, for use as a medicament.

Pharmaceutical composition, combination product or kit, as described in the preceding paragraphs, for the preventive or curative treatment of an inflammatory pulmonary disease.

The use of a PDE4 inhibitor or a pharmaceutically acceptable salt thereof and a HMG-CoA reductase inhibitor or a pharmaceutically acceptable salt thereof for the manufacture of a medicament, in particular the pharmaceutical composition according to the invention, for the preventive or curative treatment of an inflammatory pulmonary disease.

Another aspect of the present invention is the use of a PDE4 inhibitor or a pharmaceutically acceptable salt thereof and a HMG-CoA reductase inhibitor or a pharmaceutically acceptable salt thereof for the manufacture of a sequential or separate co-administrable medicament, in particular the combination product or kit according to the invention, for the preventive or curative treatment of an inflammatory pulmonary disease.

Still another aspect of the present invention is a method for the preventive or curative treatment of an inflammatory pulmonary disease comprising administering to a patient in need thereof a pharmaceutical composition comprising a pharmaceutical formulation including an amount of a PDE4 inhibitor or a pharmaceutically acceptable salt thereof, an amount of a HMG-CoA reductase inhibitor or a pharmaceutically acceptable salt thereof, wherein the first amount and the second amount together comprise an effective amount for the preventive or curative treatment of an inflammatory pulmonary disease, and at least one pharmaceutically acceptable auxiliary.

A further aspect of the present invention is a method for the preventive or curative treatment of an inflammatory pulmonary disease comprising administering to a patient in need thereof a combination product comprising the components:

(A) an amount of a PDE4 inhibitor or a pharmaceutically acceptable salt thereof;

(B) an amount of a HMG-CoA reductase inhibitor or a pharmaceutically acceptable salt thereof;

wherein the first and the second amount together comprise an effective amount for the preventive or curative treatment of an inflammatory pulmonary disease;

wherein each of the components (A) and (B) is formulated in admixture with at least one pharmaceutically acceptable auxiliary;

and wherein the components (A) and (B) are administered simultaneously, sequentially or separately.

The pharmaceutical compositions according to the invention may be prepared by mixing the first active agent with the second active agent.

In the above-mentioned mixing process the first active agent and the second active agent can a) in a first step be mixed as such, afterwards be processed with at least one pharmaceutically acceptable auxiliary and finally, for example, be pressed to tablets or caplets or b) in a first step separately be processed with at least one pharmaceutically acceptable auxiliary to give granules or pellets containing each only one of the two active agents; the pellets or granules for their part then can be mixed in an appropriate ratio and either pressed—optionally with further pharmaceutically acceptable auxiliaries—to give, for example tablets or caplets, or can be filled in loose form in capsules.

Therefore, in a still further aspect of the present invention there is provided a process for the preparation of a pharmaceutical composition which comprises mixing a first active agent, which is a PDE4 inhibitor or a pharmaceutically acceptable salt thereof with a second active agent, which is a HMG CoA-reductase inhibitor or a pharmaceutically acceptable salt thereof.

Simultaneous administration of a PDE4 inhibitor or a pharmaceutically acceptable salt thereof and a HMG-CoA reductase inhibitor or a pharmaceutically acceptable salt thereof can be preferably accomplished, by administering to the patient in need of inflammatory pulmonary disease therapy the pharmaceutical composition according to the invention in one dosage form, such as for example in a single capsule, tablet or injection.

Components (A) and (B) of the combination product as well as of the kit may be administered sequentially or separately over the course of the preventive or curative treatment of an inflammatory pulmonary disease.

Sequential or separate administration of a PDE4 inhibitor or a pharmaceutically acceptable salt thereof and a HMG-CoA reductase inhibitor or a pharmaceutically acceptable salt thereof can be preferably accomplished, by administering to the patient in need of inflammatory pulmonary disease therapy components (A) and (B) of the combination product or the kit according to the invention in (multiple) separate dosage forms, such as for example, in separate capsules, tablets or injections. The components (A) and (B) of the combination product or the kit according to the invention can also be administered simultaneously, for example by swallowing the two tablets containing the both active agents at the same time, or by using an inhaler system, which contains both active agents in separate containers, but deliver them together.

In an alternative, one of the components (A) and (B) may be formulated as tablet or capsule and the other component may be formulated for administration, for example, by injection or inhalation.

Sequential administration encompasses a short time period between the administration of components (A) and (B) of the combination product or the kit according to the invention (for example, the time that is needed to swallow one tablet after the other).

Separate administration encompasses both relatively short and relatively long time periods between the administration of components (A) and (B) of the combination product or the kit according to the invention. However, for the purposes of the present invention at least one of the components is administered while the other component is still having an effect on the patient being treated. In a preferred embodiment of the invention the effect on the patient being treated is a synergistic effect.

The combined administration of a PDE4 inhibitor or a pharmaceutically acceptable salt thereof and a HMG-CoA reductase inhibitor or a pharmaceutically acceptable salt thereof, either in form of the pharmaceutical composition, combination product or kit according to the invention, lead to an effective preventive or curative treatment of the inflammatory pulmonary disease, and in a preferred embodiment is superior to the use of either active compound alone. Moreover, in a particularly preferred embodiment, the combined administration of a PDE4 inhibitor or a pharmaceutically acceptable thereof and a HMG-CoA reductase inhibitor or a pharmaceutically acceptable salt thereof shows a synergistic efficacy for treating an inflammatory pulmonary disease.

As used herein, the term "synergistic" refers to the combination of a PDE4 inhibitor or a Pharmaceutically acceptable salt thereof with a HMG-CoA reductase inhibitor or a pharmaceutically acceptable salt thereof either in form of the pharmaceutical composition, combination product or kit according to the invention having an efficacy for the preventive or curative treatment of an inflammatory pulmonary disease that is greater than would be expected from the sum of their individuals effects. The synergistic effects of the embodiments of the present invention encompass additional unexpected advantages for the preventive or curative treatment of inflammatory pulmonary diseases. Such additional advantages may include, but are not limited to, lowering the required dose of one or more of the active compounds of the combination, reducing the side effects of one or more of the active compounds of the combination or rendering one or more of the active compounds more tolerable to the patient in need of an inflammatory pulmonary disease therapy. The combined administration of a PDE4 inhibitor or a pharmaceutically acceptable salt thereof and a HMG-CoA reductase inhibitor or a pharmaceutically acceptable salt thereof may also be useful for decreasing the required number of separate dosages, thus, potentially improving compliance of the patient in need of inflammatory pulmonary disease therapy.

The therapeutic effect of the combinations according to the invention may be also observed with regard to the fast decline in lung function that is a hallmark of COPD, and effects may be observed regarding the systemic inflammation that is also a characteristic of COPD. The long-term effect of the combinations according to the invention will be the conservation of lung function and putatively less co-morbidity (based on effects on the systemic inflammation).

The term "active compound" as used herein refers to a compound useful in the preventive or curative treatment of a disease.

The term "effective amount" as used herein refers to a therapeutically effective amount for treating an inflammatory pulmonary disease. In case of a combination therapy the term "effective amount" refers to the sum of the amounts of the combination partners, which is therapeutically effective for the preventive or curative treatment of an inflammatory pulmonary disease.

The term "patient" includes both humans and other mammals. In a preferred embodiment of the invention the term "patient" stands for humans.

The term "PDE4 inhibitor" as used herein refers to an active compound that is capable of reducing the physiological effect of the PDE4 isoenzyme of phosphodiesterase preferentially over other isoenzyme of phosphodiesterase.

Non-limiting examples of PDE4 inhibitors, which may be usefully employed in the pharmaceutical compositions, combination products and kits according to the invention are listed in Table 1.

In one embodiment of the present invention the PDE4 inhibitor is selected from the group consisting of ROFLUMILAST (CAS-No. 162401-32-3), ROFLUMILAST-N-Oxide (CAS-No. 292135-78-5), CILOMILAST (CAS-No. 153259-65-5), AWD-12-281 (CAS-No. 257892-33-4), TOFIMILAST (CAS-No. 185954-27-2), TETOMILAST (CAS-No. 145739-56-6), LIRIMILAST (CAS-No. 329306-27-6), L-869298 (CAS-No. 362718-73-8), OGLEMILAST (CAS-No. 778576-62-8), 2-{4-[(4aS,8aR)-4-(3,4-dimethoxyphenyl)-1-oxo-4a,5,8,8a-tetrahydro-1H-phthalazin-2-yl]-piperidin-1-yl}-acetamide (hereinafter referred to as COMPOUND A; CAS-No. 449760-58-1) and the pharmaceutically acceptable salts of these compounds.

In another embodiment of the present invention the PDE4 inhibitor is selected from the group consisting of ROFLUMILAST, a pharmaceutically acceptable salt of ROFLUMILAST, ROFLUMILAST-N-oxide and a pharmaceutically acceptable salt of ROFLUMILAST-N-oxide.

In another embodiment of the present invention the PDE4 inhibitor is ROFLUMILAST.

In another embodiment of the present invention the PDE4 inhibitor is ROFLUMILAST-N-oxide.

In another embodiment of the present invention the PDE4 inhibitor is CILOMILAST or a pharmaceutically acceptable salt thereof.

In another embodiment of the present invention preferred pharmaceutically acceptable salts of CILOMILAST are the lithium, sodium, ethylene diamine and tromethamine salt of CILOMILAST. A particularly preferred pharmaceutically acceptable salt of CILOMILAST is the sodium salt of CILOMILAST. Another particularly preferred pharmaceutically acceptable salt of CILOMILAST is the lithium salt of CILOMILAST. As an example for a hydrate of CILOMILAST may be mentioned the monohydrate of the lithium salt of CILOMILAST.

In another embodiment of the present invention the PDE4 inhibitor is AWD-12-281 or a pharmaceutically acceptable salt thereof.

In another embodiment of the present invention a preferred pharmaceutically acceptable salt of AWD-12-281 is the sodium salt of AWD-12-281.

In another embodiment of the present invention the PDE4 inhibitor is TOFIMILAST or a pharmaceutically acceptable salt thereof.

In another embodiment of the present invention the PDE4 inhibitor is TETOMILAST or a pharmaceutically acceptable salt thereof.

In another embodiment of the present invention the PDE4 inhibitor is LIRIMILAST or a pharmaceutically acceptable salt thereof.

In another embodiment of the present invention the PDE4 inhibitor is L-869298 or a pharmaceutically acceptable salt thereof.

In another embodiment of the present invention the PDE4 inhibitor is OGLEMILAST or a pharmaceutically acceptable salt thereof.

In another embodiment of the present invention preferred pharmaceutically acceptable salts of OGLEMILAST are the mono-sodium and the di-sodium salt of OGLEMILAST.

In another embodiment of the present invention the PDE4 inhibitor is COMPOUND A or a pharmaceutically acceptable salt thereof.

TABLE 1

| INN or Research Code | Structure/Chemical Name |
|---|---|
| ROFLUMILAST | <br>3-(cyclopropylmethoxy)-N-(3,5-dichloropyridin-4-yl)-4-(difluoromethoxy)benzamide |
| N-oxide of ROFLUMILAST = ROFLUMILAST-N-oxide | <br>3-(cyclopropylmethoxy)-N-(3,5-dichloro-1-oxidopyridin-4-yl)-4-(difluoromethoxy)benzamide |
| CILOMILAST | <br>cis-4-cyano-4-[3-(cyclopentyloxy)-4-methoxyphenyl]cyclohexanecarboxylic acid |

TABLE 1-continued

| INN or Research Code | Structure/Chemical Name |
|---|---|
| AWD-12-281 | <br>N-(3,5-dichloropyridin-4-yl)-2-[1-(4-fluorobenzyl)-5-hydroxy-1H-indol-3-yl]-2-oxoacetamide |
| TOFIMILAST | <br>9-cyclopentyl-7-ethyl-3-(2-thienyl)-6,9-dihydro-5H-pyrazolo[3,4-c][1,2,4]triazolo[4,3-a]pyridine |
| TETOMILAST | <br>6-[2-(3,4-diethoxyphenyl)-1,3-thiazol-4-yl]pyridine-2-carboxylic acid |
| LIRIMILAST | <br>3-[(aminocarbonyl)amino]-2-(2,4-dichlorobenzoyl)-1-benzofuran-6-yl methanesulfonate |

TABLE 1-continued

| INN or Research Code | Structure/Chemical Name |
|---|---|
| L-869298 | 2-{5-[(1S)-1-[3-(cyclopropyloxy)-4-(difluoromethoxy)phenyl]-2-(1-oxidopyridin-3-yl)ethyl]-1,3-thiazol-2-yl}-1,1,1,3,3,3-hexafluoropropan-2-ol |
| OGLEMILAST | N-(3,5-dichloropyridin-4-yl)-4-(difluoromethoxy)-8-[(methylsulfonyl)amino]dibenzo[b,d]furan-1-carboxamide |
| Compound A | 2-{4-[(4aS, 8aR)-4-(3,4-dimethoxyphenyl)-1-oxo-4a,5,8,8a-tetrahydro-1H-phthalazin-2-yl]-piperidin-1-yl}-acetamide |

Additional information with regard to the preparation, suitable dosage forms and dose ranges of the PDE4 inhibitors ROFLUMILAST, ROFLUMILAST-N-oxide and the pharmaceutically acceptable salts thereof can be found in the following patents/patent applications: WO9501338, WO03070279 and WO2006032676.

Additional information with regard to the preparation, suitable dosage forms and dose ranges of the PDE4 inhibitors CILOMILAST, AWD-12-281, TOFIMILAST, TETOMILAST, LIRIMILAST, L-869298, OGLEMILAST, COMPOUND A and the pharmaceutically acceptable salts thereof can be found in the following patents/patent applications: WO9319749, WO9809946, WO9955696, WO9639408, WO9209586, EP0731099, WO0170738, WO04089940 and WO02064584.

The term "HMG-CoA reductase inhibitor" as used herein refers to competitive inhibitors of 3-hydroxy-3-methylglutaryl-coenzyme A (HMG-CoA) reductase, which catalyzes an early, rate-limiting step in cholesterol biosynthesis, thereby lowering levels of cholesterol and triglyceride in hyperlipidemic patients.

Non-limiting examples of HMG-CoA reductase inhibitors, which may be usefully employed in the pharmaceutical compositions, combination products and kits according to the invention are listed in Table 2.

In one embodiment of the present invention the HMG-CoA reductase inhibitor is selected from the group consisting of LOVASTATIN (CAS-No. 75330-75-5), PRAVASTATIN (CAS-No. 081093-37-0), SIMVASTATIN (CAS-No. 079902-63-9), ATORVASTATIN (CAS-No. 134523-00-5), FLUVASTATIN (093957-54-1), ROSUVASTATIN (CAS-No. 287714-41-4), PITAVASTATIN (CAS-No. 147511-69-1), BERVASTATIN (CAS-No. 132017-01-7), DALVASTATIN (CAS-No. 132100-55-1), GLENVASTATIN (CAS-No. 122254-45-9) and the pharmaceutically acceptable salts of these compounds.

In another embodiment of the present invention the HMG-CoA reductase inhibitor is LOVASTATIN or a pharmaceutically acceptable salt thereof.

In another embodiment of the present invention the HMG-CoA reductase inhibitor is PRAVASTATIN or a pharmaceutically acceptable salt thereof.

In another embodiment of the present invention preferred pharmaceutically acceptable salts of PRAVASTATIN are the potassium, lithium, sodium and hemi-calcium salt of PRAVASTATIN. A particularly preferred pharmaceutically acceptable salt of PRAVASTATIN is the sodium salt of PRAVASTATIN.

In another embodiment of the present invention the HMG-CoA reductase inhibitor is SIMVASTATIN or a pharmaceutically acceptable salt thereof.

In another embodiment of the present invention the pharmaceutically acceptable salt of SIMVASTATIN is the sodium salt of SIMVASTATIN.

In another embodiment of the present invention the HMG-CoA reductase inhibitor is ATORVASTATIN or a pharmaceutically acceptable salt thereof.

In another embodiment of the present invention preferred pharmaceutically acceptable salts of ATORVASTATIN are the potassium, sodium and the hemi-calcium salt of ATORVASTATIN. A particularly preferred pharmaceutically acceptable salt of ATORVASTATIN is the hemi-calcium salt of ATORVASTATIN. As an example for a hydrate of ATORVASTATIN may be mentioned the trihydrate and the sesquihydrate of the hemi-calcium salt of ATORVASTATIN.

In another embodiment of the present invention the HMG-CoA reductase inhibitor is FLUVASTATIN or a pharmaceutically acceptable salt thereof.

In another embodiment of the present invention the pharmaceutically acceptable salt of FLUVASTATIN is the sodium salt of FLUVASTATIN.

In another embodiment of the present invention the HMG-CoA reductase inhibitor is ROSUVASTATIN or a pharmaceutically acceptable salt thereof.

In another embodiment of the present invention preferred pharmaceutically acceptable salts of ROSUVASTATIN are the potassium, lithium, sodium, hemi-magnesium and the hemi-calcium salt of ROSUVASTATIN. A particularly preferred pharmaceutically acceptable salt of ROSUVASTATIN is the hemi-calcium salt of ROSUVASTATIN. Another particularly preferred pharmaceutically acceptable salt of ROSUVASTATIN is the sodium salt of ROSUVASTATIN.

In another embodiment of the present invention the HMG-CoA reductase inhibitor is PITAVASTATIN or a pharmaceutically acceptable salt thereof.

In another embodiment of the present invention preferred pharmaceutically acceptable salts of PITAVASTATIN are the potassium, sodium and the hemi-calcium salt of PITAVASTATIN. A particularly preferred pharmaceutically acceptable salt of PITAVASTATIN is the hemi-calcium salt of PITAVASTATIN.

In another embodiment of the present invention the HMG-CoA reductase inhibitor is BERVASTATIN or a pharmaceutically acceptable salt thereof.

In another embodiment of the present invention the HMG-CoA reductase inhibitor is DALVASTATIN or a pharmaceutically acceptable salt thereof.

In another embodiment of the present invention the HMG-CoA reductase inhibitor is GLENVASTATIN or a pharmaceutically acceptable salt thereof.

TABLE 2

| INN or Research Code | Structure/Chemical Name |
|---|---|
| LOVASTATIN | <br>(1S,3R,7S,8S,8aR)-8-{2-[(2R,4R)-4-hydroxy-6-oxotetrahydro-2H-pyran-2-yl]ethyl}-3,7-dimethyl-1,2,3,7,8,8a-hexahydronaphthalen-1-yl (2S)-2-methylbutanoate |

TABLE 2-continued

| INN or Research Code | Structure/Chemical Name |
|---|---|
| PRAVASTATIN | <br>(3S,5R)-3,5-dihydroxy-7-[(1S,2S,6S,8S,8aR)-6-hydroxy-2-methyl-8-{[(2S)-2-methylbutanoyl]oxy}-1,2,6,7,8,8a-hexahydronaphthalen-1-yl]heptanoic acid |
| SIMVASTATIN | <br>(1R,3S,7R,8R,8aS)-8-{2-[(2R,4R)-4-hydroxy-6-oxotetrahydro-2H-pyran-2-yl]ethyl}-3,7-dimethyl-1,2,3,7,8,8a-hexahydronaphthalen-1-yl 2,2-dimethylbutanoate |
| ATORVASTATIN | <br>(3S,5R)-7-[3-(anilinocarbonyl)-5-(4-fluorophenyl)-2-isopropyl-4-phenyl-1H-pyrrol-1-yl]-3,5-dihydroxyheptanoic acid |
| FLUVASTATIN | <br>(3R,5S,6E)-7-[3-(4-fluorophenyl)-1-isopropyl-1H-indol-2-yl]-3,5-dihydroxyhept-6-enoic acid |

TABLE 2-continued

| INN or Research Code | Structure/Chemical Name |
|---|---|
| ROSUVASTATIN | <br>(3R,5R)-7-{4-(4-fluorophenyl)-6-isopropyl-2-[methyl(methylsulfonyl)amino]pyrimidin-5-yl}-3,5-dihydroxyheptanoic acid |
| PITAVASTATIN | <br>(3R,5S,6E)-7-[2-cyclopropyl-4-(4-fluorophenyl)quinolin-3-yl]-3,5-dihydroxyhept-6-enoic acid |
| BERVASTATIN | <br>Ethyl (3S,5S,6E)-7-[4-(4-fluorophenyl)spiro[chromene-2,1'-cyclopentan]-3-yl]-3,5-dihydroxyhept-6-enoate |
| DALVASTATIN | <br>(4R,6S)-6-{(E)-2-[2-(4-fluoro-3-methylphenyl)-4,4,6,6-tetramethylcyclohex-1-en-1-yl]vinyl}-4-hydroxytetrahydro-2H-pyran-2-one |

TABLE 2-continued

| INN or Research Code | Structure/Chemical Name |
|---|---|
| GLENVASTATIN | <br>(4R,6S)-6-{(E)-2-[4-(4-fluorophenyl)-2-isopropyl-6-phenylpyridin-3-yl]vinyl}-4-hydroxytetrahydro-2H-pyran-2-one |

The HMG-CoA reductase inhibitors LOVASTATIN, PRAVASTATIN, SIMVASTATIN, ATORVASTATIN, FLUVASTATIN, ROSUVASTATIN and PITAVASTATIN listed in Table 2 are commercially available. The person skilled in the art is familiar with suitable formulations and dose ranges of these compounds. Additional information with regard to the preparation, suitable dosage forms and dose ranges of these HMG-CoA reductase inhibitors and the pharmaceutically acceptable salts thereof can be found in the following patents/patent applications: EP022478, DE3122499, EP033538, EP0247633, EP0114027, EP0521471 and EP0304063.

Additional information with regard to the preparation, suitable dosage forms and dose ranges of the HMG-CoA reductase inhibitors BERVASTATIN, DALVASTATIN, GLENVASTATIN and the pharmaceutically acceptable salts thereof can be found in the following patents/patent applications: EP0380392, WO8905639 and EP0307342.

Salts encompassed within the term "pharmaceutically acceptable salts" are not restricted to the specific examples given above. The term refers to non-toxic salts of the PDE4 inhibitors or the HMG-CoA reductase inhibitors, which are generally prepared by reacting a free base with a suitable organic or inorganic acid (acid addition salt) or by reacting the free acid with a suitable organic or inorganic base. Acid addition salts include, but are not limited to, hydrochlorides, hydrobromides, phosphates, nitrates, sulfates, acetates, citrates, D-gluconates, benzoates, 2-(4-hydroxybenzoyl)benzoates, butyrates, sulfosalicylates, maleates, laurates, malates, fumarates, succinates, oxalates, tartarates, stearates, toluenesulfonates, methanesulfonates, 3-hydroxy-2-naphthoates and trifluoroacetates. Examples of salts with bases include, but are not limited to, lithium, sodium, potassium, calcium, aluminum, magnesium, titanium, ammonium, meglumine and guanidinium salts.

It is understood that the PDE4 inhibitors, the HMG-CoA reductase inhibitors as well as their pharmaceutically acceptable salts can also be present in the form of their pharmaceutically acceptable solvates and in particular in the form of their pharmaceutically acceptable hydrates.

The combinations according to the invention may be administered by any suitable route, for example, by the oral, sublingual, buccal, intravenous, intraarterial, intramuscular, subcutaneous, intracutaneous, topical, transdermal, intranasal, intraperitoneal, rectal or vaginal route, by inhalation or by insufflation.

Tablets, coated tablets (dragees), pills, cachets, capsules (caplets), granules, solutions, emulsions and suspensions are e.g. suitable for oral administration. In particular, said formulations can be adapted so as to represent, for example, an enteric form, an immediate release form, a delayed release form, a repeated dose release form, a prolonged release form or a sustained release form. Said forms can be obtained, for example, by coating tablets, by dividing tablets into several compartments separated by layers disintegrating under different conditions (e.g. pH conditions) or by coupling the active compound to a biodegradable polymer.

Administration by inhalation is preferably made by using an aerosol. The aerosol is a liquid-gaseous dispersion, a solid-gaseous dispersion or a mixed liquid/solid-gaseous dispersion.

The aerosol may be generated by means of aerosol-producing devices such as dry powder inhalers (DPIs), pressurized metered dose inhalers (PMDIs) and nebulizers. Depending on the kind of the active compound to be administered, the aerosol-producing device can contain the active compound in form of a powder, a solution or a dispersion. The powder may contain, for example, one or more of the following auxiliaries: carriers, stabilizers and fillers. The solution may contain in addition to the solvent, for example, one or more of the following auxiliaries: propellants, solubilizers (co-solvents), surfactants, stabilizers, buffers, tonicity adjusting agents, preservatives and flavorings. The dispersion may contain in addition to the dispersant, for example, one or more of the following auxiliaries: propellants, surfactants, stabilizers, buffers, preservatives and flavorings. Examples of carriers include, but are not limited to, saccharides, e.g. lactose and glucose. Examples of propellants include, but are not limited to, fluorohydrocarbons, e.g. 1,1,1,2-tetrafluoroethane and 1,1,1,2,3,3,3-heptafluoropropane.

The particle size of the aerosol particles (solid, liquid or solid/liquid particles) is preferably less than 100 μm, more preferably it is in the range of from 0.5 to 10 μm, in particular in the range of from 2 to 6 μm (D50 value, measured by laser diffraction).

For parenteral modes of administration such as, for example, intravenous, intraarterial, intramuscular, subcutaneous, intracutaneous and intraperitoneal administration, preferably solutions (e.g. sterile solutions, isotonic solutions) are used. They are preferably administered by injection or infusion techniques.

The pharmaceutical compositions (formulations) comprising the PDE4 inhibitor or a pharmaceutically acceptable salt thereof and/or the HMG CoA reductase inhibitor or a pharmaceutically acceptable salt thereof and at least one pharmaceutically acceptable auxiliary can be manufactured in a manner known to a person skilled in the art, e.g. by dissolving, mixing, granulating, dragee-making, levigating, emulsifying, encapsulating, entrapping or lyophilizing processes. As pharmaceutically acceptable auxiliaries, any auxiliaries known to be suitable for preparing pharmaceutical compositions (formulations) can be used. Examples thereof include, but are not limited to, solvents, excipients, dispersants, emulsifiers, solubilizers, gel formers, ointment bases, antioxidants, preservatives, stabilizers, carriers, fillers, binders, thickeners, complexing agents, disintegrating agents, buffers, permeation promoters, polymers, lubricants, coating agents, propellants, tonicity adjusting agents, surfactants, colorants, flavorings, sweeteners and dyes. In particular, auxiliaries of a type appropriate to the desired formulation and the desired mode of administration are used.

The most preferred mode of administration of Roflumilast, Roflumilast-N-oxide or a pharmaceutically acceptable salt of either is oral. In another preferred embodiment Roflumilast, Roflumilast-N-oxide or a pharmaceutically acceptable salt of either is administered by intravenous infusion or injection. In a further embodiment Roflumilast, Roflumilast-N-oxide or a pharmaceutically acceptable salt of either is administered by intramuscular or subcutaneous injection. Other routes of administration are also contemplated, including for example intranasal and transdermal routes, and by inhalation.

The preferred mode of administration of the PDE4 inhibitors CILOMILAST, TETOMILAST, LIRIMILAST, L-869298, OGLEMILAST and COMPOUND A is oral, while the preferred mode of administration of the PDE4 inhibitors AWD-12-281 and TOFIMILAST is administration by inhalation.

The preferred mode of administration of the HMG CoA reductase inhibitors LOVASTATIN, PRAVASTATIN; SIMVASTATIN; ATORVASTATIN, FLUVASTATIN, ROSUVASTATIN, PITAVASTATIN, BERVASTATIN, DALVASTATIN and GLENVASTATIN is oral.

The exact dosage and regimen for administering a PDE4 inhibitor or a pharmaceutically acceptable salt thereof in combination with a HMG-CoA reductase inhibitor or a pharmaceutically acceptable salt thereof will necessarily depend on the potency and duration of action of the active compounds used, the nature and severity of the inflammatory pulmonary disease to be treated, as well as the sex, age, weight, general health and individual responsiveness of the patient to be treated, and other relevant circumstances.

As part of the combination therapy according to the invention the PDE4 inhibitor or a pharmaceutically acceptable salt thereof and the HMG-CoA reductase inhibitor or a pharmaceutically acceptable salt thereof are dosed in an order of magnitude customary for the mono-therapy, it more likely being possible, on account of the individual actions, which are mutually positively influencing and reinforcing, to reduce the respective doses on the combined administration of the PDE4 inhibitor or a pharmaceutically acceptable salt thereof and the HMG-CoA reductase inhibitor or a pharmaceutically acceptable salt thereof with the norm.

Without intended to be limiting, the orally administered daily dosage (for an adult patient) of the PDE4 inhibitors or the pharmaceutically acceptable salts thereof will generally range from about 0.05 mg to about 200 mg; without intended to be limiting, the daily dosage (for an adult patient) of a PDE4 inhibitor or a pharmaceutically acceptable salt thereof for administration by inhalation will generally range from 0.05 mg to about 100 mg.

In the case of oral administration of 3-cyclopropyl-methoxy-4-difluoromethoxy-N-(3,5-dichloropyrid-4-yl) benzamide (ROFLUMILAST) the daily dose (for an adult patient) for the mono-therapy is in the range from 50 to 1000 μg per day, preferably in the range of 50 to 500 μg per day, preferably by once daily administration. In the case of intravenous administration of 3-cyclopropylmethoxy-4-difluoromethoxy-N-(3,5-dichloropyrid-4-yl)benzamide (ROFLUMILAST) the daily dose (for an adult patient) for the mono-therapy is in the range from 50 to 500 μg per day, preferably 150 to 300 μg per day.

In the case of oral administration of CILOMILAST the daily dose (for an adult patient) for the mono-therapy is likely to be in the range from 10 to 40 mg per day, preferably from 20 to 30 mg per day, preferably by twice daily administration.

In the case of administration by inhalation of AWD-12-281 the daily dosage (for an adult patient) for the mono-therapy is likely to be in the range of 500 to 2000 μg per day.

In the case of oral administration of LIRIMILAST the daily dosage (for an adult patient) for the mono-therapy is likely to be in a range of 1 to 10 mg per day.

In the case of oral administration of OGLEMILAST the daily dosage (for an adult patient) for the mono-therapy is likely to be in the range of 1 to 10 mg per day.

In the case of oral administration of COMPOUND A the daily dosage (for an adult patient) for the mono-therapy is likely to be in a range of 0.1 to 10 mg once daily, preferably 0.1 to 2 mg once daily.

The orally administered daily dosage (for an adult patient) of the HMG-CoA reductase inhibitors or the pharmaceutically acceptable salts thereof will generally range from about 0.01 mg to about 200 mg, preferably from 10 to 80 mg, more preferably from 5 to 40 mg; for administration by inhalation a dosage range of 0.001 mg to about 25 mg is preferred, even more preferable is a dosage from 0.1 to 25 mg.

TABLE 3

Preferred Combinations

| Example Number | Combination | |
|---|---|---|
| 1 | ROFLUMILAST | LOVASTATIN |
| 2 | ROFLUMILAST-N-Oxide | LOVASTATIN |
| 3 | ROFLUMILAST | PRAVASTATIN |
| 4 | ROFLUMILAST-N-Oxide | PRAVASTATIN |
| 5 | ROFLUMILAST | PRAVASTATIN sodium |
| 6 | ROFLUMILAST-N-Oxide | PRAVASTATIN sodium |
| 7 | ROFLUMILAST | SIMVASTATIN |
| 8 | ROFLUMILAST-N-Oxide | SIMVASTATIN |
| 9 | ROFLUMILAST | ATORVASTATIN |
| 10 | ROFLUMILAST-N-Oxide | ATORVASTATIN |
| 11 | ROFLUMILAST | ATORVASTATIN hemi-calcium sesqui-hydrate |
| 12 | ROFLUMILAST-N-Oxide | ATORVASTATIN hemi-calcium sesqui-hydrate |
| 13 | ROFLUMILAST | FLUVASTATIN |

TABLE 3-continued

Preferred Combinations

| Example Number | Combination | |
|---|---|---|
| 14 | ROFLUMILAST-N-Oxide | FLUVASTATIN |
| 15 | ROFLUMILAST | FLUVASTATIN sodium |
| 16 | ROFLUMILAST-N-Oxide | FLUVASTATIN sodium |
| 17 | ROFLUMILAST | ROSUVASTATIN |
| 18 | ROFLUMILAST-N-Oxide | ROSUVASTATIN |
| 19 | ROFLUMILAST | ROSUVASTATIN hemi-calcium |
| 20 | ROFLUMILAST-N-Oxide | ROSUVASTATIN hemi-calcium |
| 21 | ROFLUMILAST | ROSUVASTATIN sodium |
| 22 | ROFLUMILAST-N-Oxide | ROSUVASTATIN sodium |
| 23 | ROFLUMILAST | PITAVASTATIN |
| 24 | ROFLUMILAST-N-Oxide | PITAVASTATIN |
| 25 | ROFLUMILAST | PITAVASTATIN hemi-calcium |
| 26 | ROFLUMILAST-N-Oxide | PITAVASTATIN hemi-calcium |
| 27 | ROFLUMILAST | BERVASTATIN |
| 28 | ROFLUMILAST-N-Oxide | BERVASTATIN |
| 29 | ROFLUMILAST | DALVASTATIN |
| 30 | ROFLUMILAST-N-Oxide | DALVASTATIN |
| 31 | ROFLUMILAST | GLENVASTATIN |
| 32 | ROFLUMILAST-N-Oxide | GLENVASTATIN |
| 33 | CILOMILAST | LOVASTATIN |
| 34 | CILOMILAST | PRAVASTATIN |
| 35 | CILOMILAST | PRAVASTATIN sodium |
| 36 | CILOMILAST | SIMVASTATIN |
| 37 | CILOMILAST | ATORVASTATIN |
| 38 | CILOMILAST | ATORVASTATIN hemi-calcium sesqui-hydrate |
| 39 | CILOMILAST | FLUVASTATIN |
| 40 | CILOMILAST | FLUVASTATIN sodium |
| 41 | CILOMILAST | ROSUVASTATIN |
| 42 | CILOMILAST | ROSUVASTATIN hemi-calcium |
| 43 | CILOMILAST | ROSUVASTATIN sodium |
| 44 | CILOMILAST | PITAVASTATIN |
| 45 | CILOMILAST | PITAVASTATIN hemi-calcium |
| 46 | CILOMILAST | BERVASTATIN |
| 47 | CILOMILAST | DALVASTATIN |
| 48 | CILOMILAST | GLENVASTATIN |
| 49 | AWD-12-281 | LOVASTATIN |
| 50 | AWD-12-281 | PRAVASTATIN |
| 51 | AWD-12-281 | PRAVASTATIN sodium |
| 52 | AWD-12-281 | SIMVASTATIN |
| 53 | AWD-12-281 | ATORVASTATIN |
| 54 | AWD-12-281 | ATORVASTATIN hemi-calcium sesqui-hydrate |
| 55 | AWD-12-281 | FLUVASTATIN |
| 56 | AWD-12-281 | FLUVASTATIN sodium |
| 57 | AWD-12-281 | ROSUVASTATIN |
| 58 | AWD-12-281 | ROSUVASTATIN hemi-calcium |
| 59 | AWD-12-281 | ROSUVASTATIN sodium |
| 60 | AWD-12-281 | PITAVASTATIN |
| 61 | AWD-12-281 | PITAVASTATIN hemi-calcium |
| 62 | AWD-12-281 | BERVASTATIN |
| 63 | AWD-12-281 | DALVASTATIN |
| 64 | AWD-12-281 | GLENVASTATIN |
| 65 | TOFIMILAST | LOVASTATIN |
| 66 | TOFIMILAST | PRAVASTATIN |
| 67 | TOFIMILAST | PRAVASTATIN sodium |
| 68 | TOFIMILAST | SIMVASTATIN |
| 69 | TOFIMILAST | ATORVASTATIN |
| 70 | TOFIMILAST | ATORVASTATIN hemi-calcium sesqui-hydrate |
| 71 | TOFIMILAST | FLUVASTATIN |
| 72 | TOFIMILAST | FLUVASTATIN sodium |
| 74 | TOFIMILAST | ROSUVASTATIN |
| 75 | TOFIMILAST | ROSUVASTATIN hemi-calcium |
| 76 | TOFIMILAST | ROSUVASTATIN sodium |
| 77 | TOFIMILAST | PITAVASTATIN |
| 78 | TOFIMILAST | PITAVASTATIN hemi-calcium |
| 79 | TOFIMILAST | BERVASTATIN |
| 80 | TOFIMILAST | DALVASTATIN |
| 81 | TOFIMILAST | GLENVASTATIN |
| 82 | TETOMILAST | LOVASTATIN |
| 83 | TETOMILAST | PRAVASTATIN |
| 84 | TETOMILAST | PRAVASTATIN sodium |
| 85 | TETOMILAST | SIMVASTATIN |
| 86 | TETOMILAST | ATORVASTATIN |
| 87 | TETOMILAST | ATORVASTATIN hemi-calcium sesqui-hydrate |
| 88 | TETOMILAST | FLUVASTATIN |
| 89 | TETOMILAST | FLUVASTATIN sodium |
| 90 | TETOMILAST | ROSUVASTATIN |
| 91 | TETOMILAST | ROSUVASTATIN hemi-calcium |
| 92 | TETOMILAST | ROSUVASTATIN sodium |
| 93 | TETOMILAST | PITAVASTATIN |
| 94 | TETOMILAST | PITAVASTATIN hemi-calcium |
| 95 | TETOMILAST | BERVASTATIN |
| 96 | TETOMILAST | DALVASTATIN |
| 97 | TETOMILAST | GLENVASTATIN |
| 98 | OGLEMILAST | LOVASTATIN |
| 99 | OGLEMILAST | PRAVASTATIN |
| 100 | OGLEMILAST | PRAVASTATIN sodium |
| 101 | OGLEMILAST | SIMVASTATIN |
| 102 | OGLEMILAST | ATORVASTATIN |
| 103 | OGLEMILAST | ATORVASTATIN hemi-calcium sesqui-hydate |
| 104 | OGLEMILAST | FLUVASTATIN |
| 105 | OGLEMILAST | FLUVASTATIN sodium |
| 106 | OGLEMILAST | ROSUVASTATIN |
| 107 | OGLEMILAST | ROSUVASTATIN hemi-calcium |
| 108 | OGLEMILAST | ROSUVASTATIN sodium |
| 109 | OGLEMILAST | PITAVASTATIN |
| 110 | OGLEMILAST | PITAVASTATIN hemi-calcium |
| 111 | OGLEMILAST | BERVASTATIN |
| 112 | OGLEMILAST | DALVASTATIN |
| 113 | OGLEMILAST | GLENVASTATIN |
| 114 | COMPOUND A | LOVASTATIN |
| 115 | COMPOUND A | PRAVASTATIN |
| 116 | COMPOUND A | PRAVASTATIN sodium |
| 117 | COMPOUND A | SIMVASTATIN |
| 118 | COMPOUND A | ATORVASTATIN |
| 119 | COMPOUND A | ATORVASTATIN hemi-calcium sesqui-hydate |
| 120 | COMPOUND A | FLUVASTATIN |
| 121 | COMPOUND A | FLUVASTATIN sodium |
| 122 | COMPOUND A | ROSUVASTATIN |
| 123 | COMPOUND A | ROSUVASTATIN hemi-calcium |
| 124 | COMPOUND A | ROSUVASTATIN sodium |
| 125 | COMPOUND A | PITAVASTATIN |
| 126 | COMPOUND A | PITAVASTATIN hemi-calcium |
| 127 | COMPOUND A | BERVASTATIN |
| 128 | COMPOUND A | DALVASTATIN |
| 129 | COMPOUND A | GLENVASTATIN |

Pharmacology:

Synergistic Inhibition of LPS-Induced Systemic TNFα Release in Rats by a Combination of ATORVASTATIN Hemi-Calcium Sesqui-Hydrate and 2-{4-[(4aS,8aR)-4-(3,4-dimethoxyphenyl)-1-oxo-4a,5,8,8a-tetrahydro-1H-phthalazin-2-yl]-piperidin-1-yl}-acetamide (COMPOUND A)

Animals:
  male Sprague Dawley rats 200-280 g

Drugs:
  ATORVASTATIN hemi-calcium sesqui-hydrate (Alexis Pharmaceuticals, San Diego, Calif., USA) and COMPOUND A (ALTANA Pharma, Konstanz, Germany).

Methods:
  Drugs were administered by gavage as a methocel/polyethylenglycol 400 suspension 1 h before intravenous administration of LPS (0.1 mg/kg). Euthanasia was induced 90 minutes later by injecting pentobarbital (48 mg/kg) and heparin (1,000 U/kg). Heparinized blood was obtained by heart puncture. Blood was centrifuged (21,000×g, 4° C., 15 min), and plasma samples were kept frozen at −80° C. until determination of TNFα levels by a commercially available ELISA kit (Quantakine®M, Rat TNFα immunoassay, R&D, MN, USA).

Statistics:

All data are given as mean±SEM. Significances were calculated on the primary TNFα concentrations in comparison with the LPS-challenged control group using ANOVA with subsequent Dunnett's Test provided by GraphPadPrism software package. Differences with $p<0.05$ were considered significant. Dose-response curves were calculated by non-linear regression analysis within fixed limits of 0 to 100% inhibition. 50% inhibitory dose ($ED_{50}$) values were derived from dose-response curves.

Figure 1:
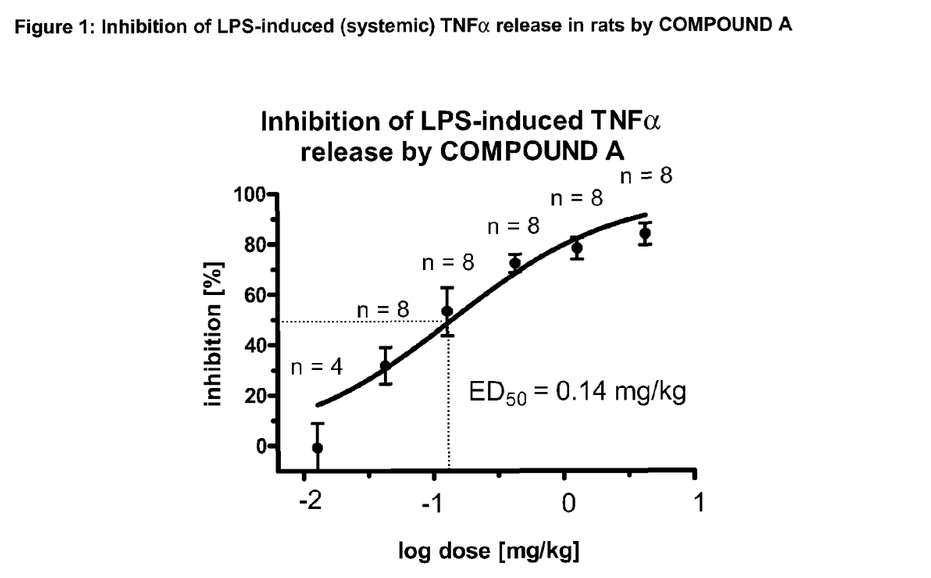
FIG. 1: Inhibition of LPS-induced (systemic) TNFα release in rats by COMPOUND A
Figure 2:
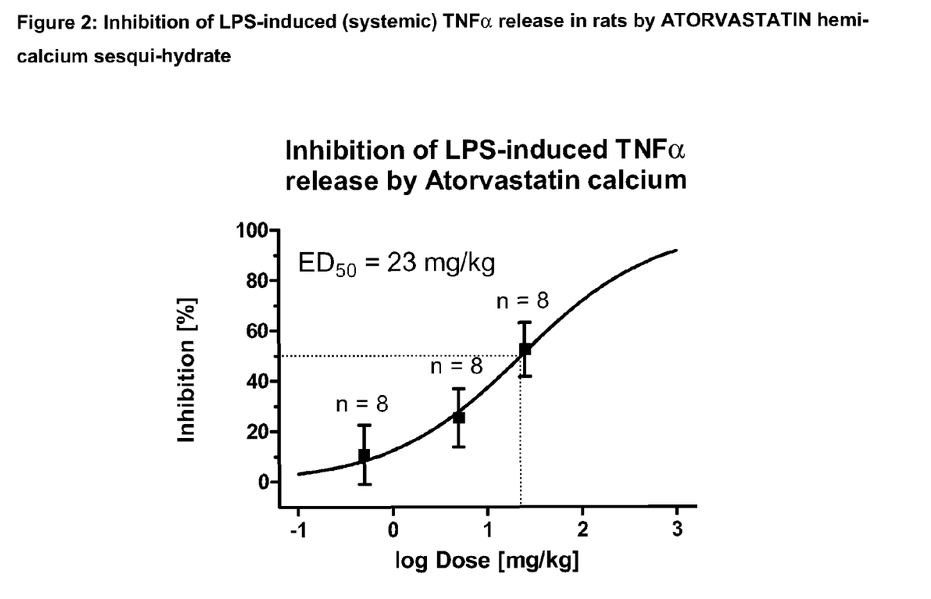
FIG. 2: Inhibition of LPS-induced (systemic) TNFα release in rats by ATORVASTATIN hemi-calcium sesqui-hydrate
Figure 3:
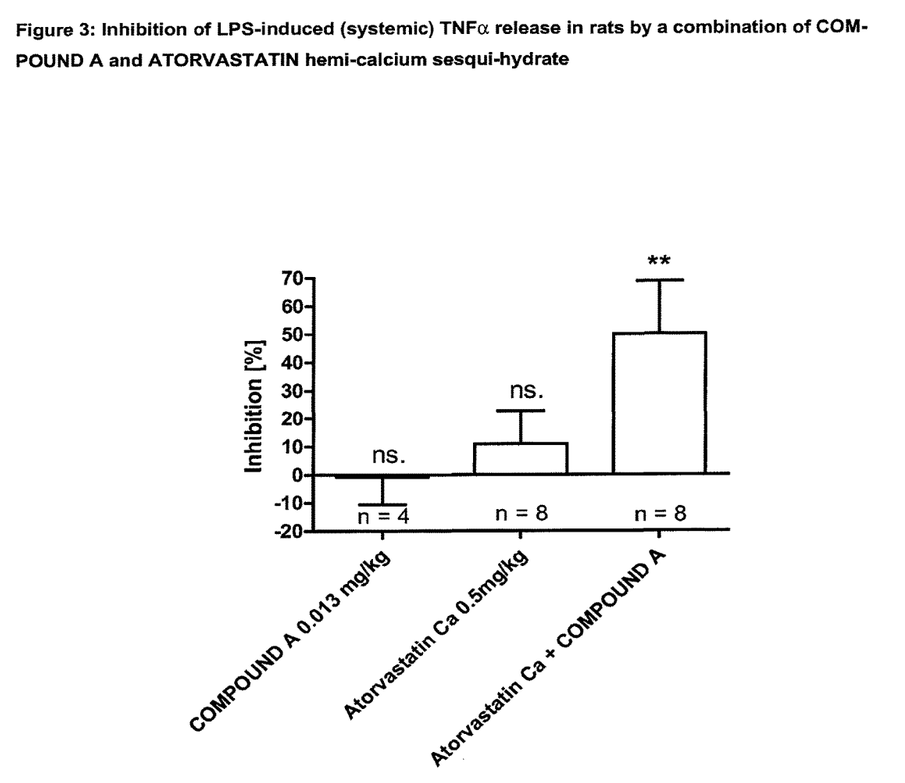
FIG. 3: Inhibition of LPS-induced (systemic) TNFα release in rats by a combination of COMPOUND A and ATORVASTATIN hemi-calcium sesqui-hydrate

Results:

LPS-induced systemic TNFα release was dose dependently inhibited by COMPOUND A and ATORVASTATIN calcium with $ED_{50}$ values of 0.14 mg/kg (FIG. 1) and 23 mg/kg (FIG. 2), respectively. COMPOUND A at a dose of 0.013 mg/kg (1% increase versus placebo) as well as ATORVASTATIN hemi-calcium sesqui-hydrate at a dose of 0.5 mg/kg (11% decrease versus placebo) showed no significant effects. However combination of COMPOUND A (0.13 mg/kg) with ATORVASTATIN hemi-calcium sesqui-hydrate (0.5 mg/kg) unexpectedly led to a significant inhibition of >50% ($P<0.01$).

Conclusion:

The combination of sub-effective doses of the PDE4 inhibitor COMPOUND A and the HMG-CoA reductase inhibitor ATORVASTATIN hemi-calcium sesqui-hydrate unexpectedly showed a potent (synergistic) and effective inhibition of inflammatory processes.

DESCRIPTION OF THE FIGURES

In the figures ATORVASTATIN hemi-calcium sesqui-hydrate is indicated simply as "ATORVASTATIN Ca"

The invention claimed is:

1. A method for the treatment of an inflammatory pulmonary disease comprising administering to a patient in need thereof a pharmaceutical composition comprising a pharmaceutical formulation including
an active ingredient combination consisting of a first amount of a PDE4 inhibitor or a pharmaceutically acceptable salt thereof, and a second amount of a HMG-CoA reductase inhibitor or a pharmaceutically acceptable salt thereof,
and at least one pharmaceutically acceptable auxiliary,
wherein the PDE4 inhibitor is selected from the group consisting of ROFLUMILAST, ROFLUMILAST-N-oxide, and pharmaceutically acceptable salts of those compounds,
wherein the HMG-CoA reductase inhibitor is selected from the group consisting of ROSUVASTATIN and pharmaceutically acceptable salts of ROSUVASTATIN, and
wherein the active ingredient combination is present in an effective amount for the treatment of an inflammatory pulmonary disease.

2. A method for the treatment of an inflammatory pulmonary disease comprising administering to a patient in need thereof one or more pharmaceutical formulations jointly including, as active agent components:
(A) a first amount of a PDE4 inhibitor; and
(B) a second amount of a HMG-CoA reductase inhibitor;
wherein the PDE4 inhibitor is selected from the group consisting of ROFLUMILAST, ROFLUMILAST-N-oxide, and pharmaceutically acceptable salts of those compounds,
wherein the HMG-CoA reductase inhibitor is selected from the group consisting of ROSUVASTATIN and pharmaceutically acceptable salts of ROSUVASTATIN,
wherein the active agent components consist of the PDE4 inhibitor and the HMG-CoA reductase inhibitor in amounts that jointly are effective for the treatment of an inflammatory pulmonary disease; and
wherein the components (A) and (B) are administered simultaneously, sequentially or separately.

3. The method according to claim 1, wherein the PDE4 inhibitor is ROFLUMILAST and the HMG-CoA reductase inhibitor is ROSUVASTATIN.

4. The method according to claim 2, wherein the PDE4 inhibitor is ROFLUMILAST and the HMG-CoA reductase inhibitor is ROSUVASTATIN.

5. The method according to claim 2, wherein the inflammatory pulmonary disease is selected from the group consisting of asthma, COPD, sclerosis, alveolitis, sarcoidosis, idiopathic pulmonary fibrosis and pulmonary hypertension.

6. The method according to claim 2, wherein the inflammatory pulmonary disease is COPD.

* * * * *